(12) United States Patent
Roe

(10) Patent No.: US 8,546,641 B2
(45) Date of Patent: Oct. 1, 2013

(54) HIGH-CAPACITY DISPOSABLE ABSORBENT INSERTS FOR REUSABLE OUTER COVERS

(75) Inventor: Donald Carroll Roe, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 375 days.

(21) Appl. No.: 12/841,600

(22) Filed: Jul. 22, 2010

(65) Prior Publication Data

US 2012/0022492 A1    Jan. 26, 2012

(51) Int. Cl.
*A61F 13/15*    (2006.01)
*A61F 13/20*    (2006.01)

(52) U.S. Cl.
USPC .. 604/378; 604/367; 604/385.01; 604/385.14

(58) Field of Classification Search
USPC ................ 604/385.01, 367, 374, 378, 385.14
See application file for complete search history.

(56) References Cited

U.S. PATENT DOCUMENTS

| | | | |
|---|---|---|---|
| 5,360,422 A | 11/1994 | Brownlee et al. | |
| 5,458,591 A | 10/1995 | Roessler et al. | |
| 5,509,915 A * | 4/1996 | Hanson et al. | 604/378 |
| 2002/0143316 A1 | 10/2002 | Sherrod | |
| 2006/0095012 A1* | 5/2006 | Cohen | 604/367 |
| 2010/0179495 A1 | 7/2010 | Roe | |

FOREIGN PATENT DOCUMENTS

| | | |
|---|---|---|
| EP | 0667136 | 8/1995 |
| WO | WO 2010078661 | 7/2010 |

OTHER PUBLICATIONS

PCT International Search Report, PCT/US2011/044667 date of mailing Oct. 20, 2011.

* cited by examiner

*Primary Examiner* — Michele M Kidwell
(74) *Attorney, Agent, or Firm* — Christian M. Best; Charles R. Ware

(57) ABSTRACT

High-capacity disposable absorbent inserts for reusable outer covers.

16 Claims, 5 Drawing Sheets

HIGH-CAPACITY DISPOSABLE ABSORBENT INSERTS FOR REUSABLE OUTER COVERS

FIELD OF THE INVENTION

The present invention relates generally to the field of diapers and more particularly, to high-capacity disposable absorbent inserts for use with reusable outer covers.

BACKGROUND OF THE INVENTION

Several designs of diapers include a reusable outer cover been manufactured and marketed. However, these designs have low-capacity absorbent inserts.

DETAILED DESCRIPTION OF THE INVENTION

Definitions

Figure 1:
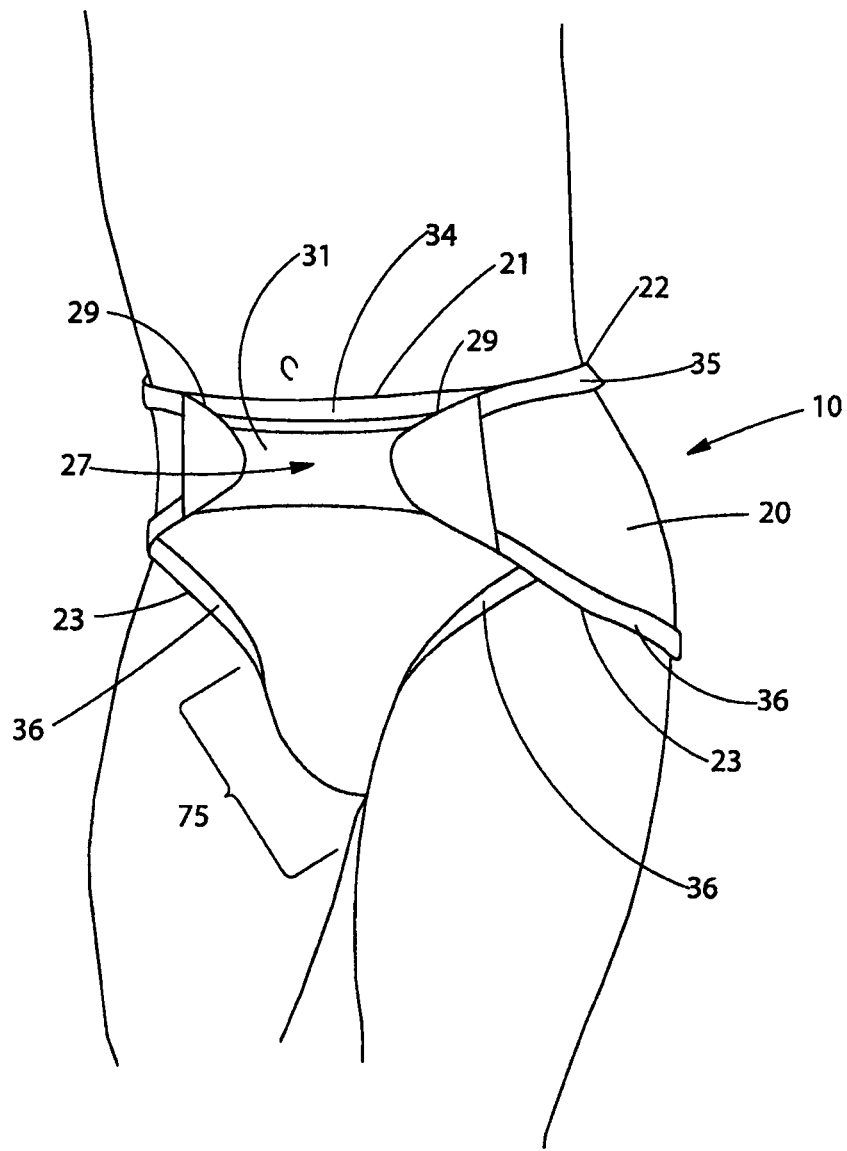
FIG. 1 is a perspective view of a wearable absorbent article as it might appear being worn by a wearer about the lower torso.

For purposes of this description, the following terms have the meanings set forth:

"Absorbent insert" and "insert" mean a component of a wearable absorbent article that is adapted to contain and/or absorb urine, feces, menses or any combination thereof, and is adapted to be installable and removable as a modular unit, from an outer cover. Herein, an absorbent insert may also be referred to as an "absorbent assembly". The terms "absorbent insert," "insert" and "absorbent assembly" may be used interchangeably herein.

"Chassis" means a component of a wearable absorbent article that is adapted to be worn about the lower torso of a wearer, and is adapted to support an absorbent insert and hold the insert next to the wearer's body. Herein, a chassis may also be referred to as an "outer cover". The terms "outer cover" and "chassis" are interchangeable for purposes herein.

"Disposable", when referring to an absorbent insert, means that the absorbent insert is not adapted or intended to be effectively sanitarily laundered in an ordinary household laundering process and ordinary household equipment, and thereby is ordinarily unsuitable for sanitary and effective reuse so as to provide as-new intended functions and performance, following soiling by exudates and removal from an outer cover. By way of non-limiting examples, effective laundering may be frustrated or prevented, causing the insert to be disposable, by inclusion of materials and/or construction: that do not retain their substantial as-new physical shape or structure through ordinary household laundering and drying so as to be effective as-new in reuse; that absorb aqueous liquids and cannot be sufficiently dried/dehydrated in ordinary household drying equipment and ordinary drying cycles so as to be effective as-new in reuse; that dissolve or substantially degrade in ordinary household laundering or drying, causing the insert to be substantially damaged or rendered useless; and/or that cannot be effectively cleaned of exudate material through ordinary laundering, so as to be sanitary and otherwise acceptable for re-use.

"Fastener component" means any component of a system that effects removable fastening, attachment or holding of a first structure to a second structure. The system may have a single fastener component, for example, an adhesive patch on the first structure adapted to adhere to one or more types of surfaces on the second structure, or a hook, or patch of hooks on the first structure, adapted to catch on one or more types of surfaces on the second structure. By way of further example, any structure such as a pocket, strap, hook, buckle, etc. on a first structure adapted to capture and retain, in whole or in part, the second structure, is a "fastener component" as used herein. The system also may comprise two or more fastener components, for example, respective components of a hook-and-loop fastening system (such as VELCRO), respective surfaces having a cohesive material applied thereto; male and female snap fastener components, a button and button hole, slot or loop, other fastenably cooperating elements, etc. Other examples of fastener components include zipper components, "zip lock" engaging components, loops, posts, pockets, bands or straps, microfasteners, macrofasteners, and fastener components such as described in U.S. Pat. Nos. 6,936,039; 6,893,388; 6,669,618; 6,432,098; and 6,251,097, and U.S. Published Applications, Pub. Nos. 2005/0234419; 2005/0215971; 2005/0215970; 2005/0130821; 2004/0023771; 2003/0233082; 2003/0119641; 2003/0088220; and 2002/0169431.

"Lateral" (and forms thereof), with respect to a wearer, means along a direction generally transverse or across the direction extending from the front to the rear of the wearer, or vice versa. With respect to a component of a wearable absorbent article, "lateral" (and forms thereof), means along a direction generally transverse or across the direction extending along the component as it would be properly situated on a wearer, from the front to the rear of the wearer, or vice versa.

"Longitudinal" (and forms thereof), with respect to a wearer, means along a direction generally extending from the front to the rear of the wearer, or vice versa. With respect to a component of a wearable absorbent article, "longitudinal" (and forms thereof), means along a direction generally extending along the component as it would be properly situated on a wearer, from the front to the rear of the wearer, or vice versa.

"Outer cover" means a component of a wearable absorbent article that is adapted to be worn about the lower torso of a wearer, and is adapted to support an absorbent insert and hold the insert next to the wearer's body. Herein, an outer cover may also be referred to as a "chassis". The terms "outer cover" and "chassis" are interchangeable for purposes herein.

"Reusable", when referring to an outer cover, means an outer cover that is adapted to permit removal of at least a first insert, and replacement thereof with at least a second insert, without substantial destruction of any components of the outer cover that are necessary to provide the substantial as-new functionality of the outer cover, and without the necessity of any repair or reconstruction following such insert replacement.

"Use," with respect to an outer cover, means one event of the wearing of the outer cover until the time an absorbent insert is replaced.

"User" means a caregiver or other person who may apply a wearable absorbent article to a wearer. Where the wearer is capable of donning the wearable absorbent article him/herself, the wearer is also a "user".

"Wearer" means a person who may wear a wearable absorbent article as described herein.

"Wearable absorbent article" means any article designed to be worn about the lower torso and to contain and/or absorb urine, feces, menses or any combination thereof "Wearable absorbent article" includes but is not limited to baby or children's diapers (of the "tape"-fastenable, otherwise fastenable, "pull-up" or any other variety), training pants and adult incontinence pants, briefs and the like.

Two-Piece Wearable Absorbent Articles

FIG. 1 depicts an example of a wearable absorbent article 10 having certain features, as it might appear while being worn by a wearer. Wearable absorbent article 10 may include an outer cover 20, having front waist edge 21, rear waist edge 22, and a pair of leg opening edges 23.

Figure 2A:
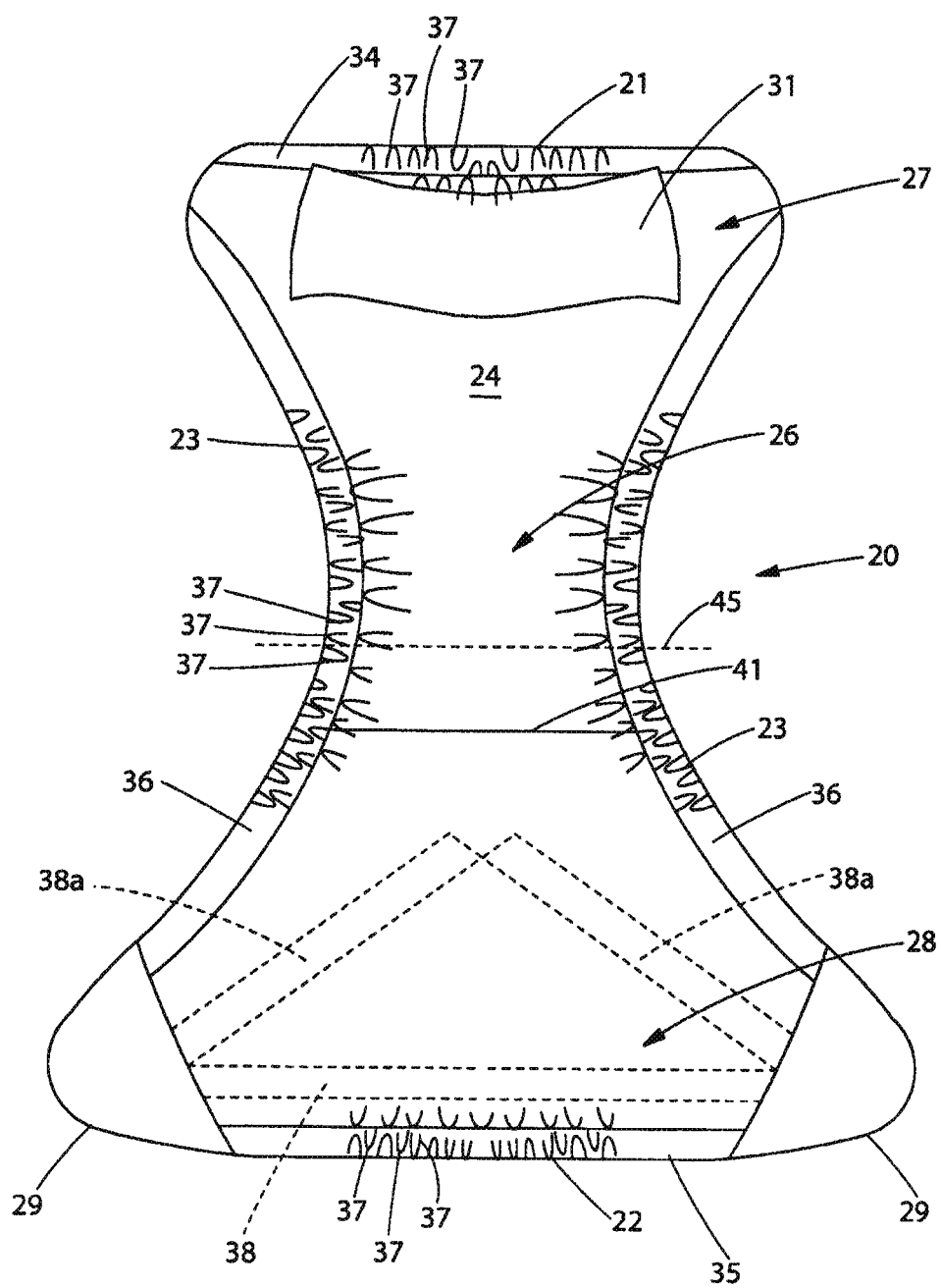
FIG. 2A is a plan view of an outer cover opened and laid flat, outer surface facing the viewer.
Figure 2B:
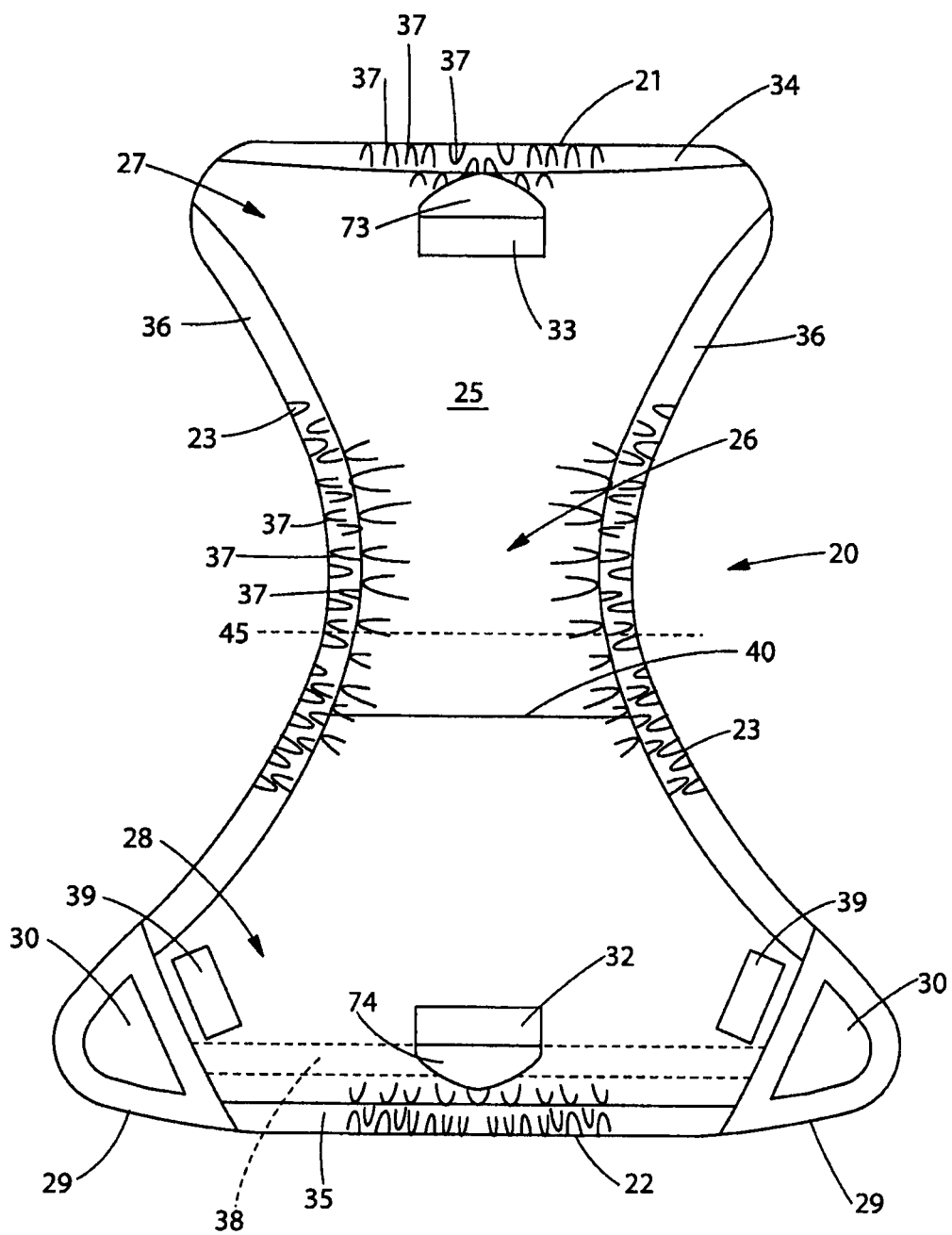
FIG. 2B is a plan view of an outer cover opened and laid flat, inner surface facing the viewer.

FIGS. 2A and 2B depict an outer cover 20 as it may appear opened and laid flat. In FIG. 2A, the outer, i.e., garment-facing, surfaces of outer cover 20 face the viewer; in FIG. 2B, the inner, i.e., wearer-facing, surfaces of outer cover 20 face the viewer. Front and rear waist edges 21, 22 are depicted at the top and bottom of the drawings, respectively. Outer cover 20 may have crotch region 26, front region 27, rear region 28 and a pair of fastening ears 29 laterally extending from rear region 28. Outer cover 20 will have a length LC from the forwardmost portion of front waist edge 21 to the rearwardmost portion of rear waist edge 22, and an outer cover lateral axis 45 equally dividing this length. Thus, front region 27 is forward of outer cover lateral axis 45, and rear region 28 is rearward of outer cover lateral axis 45. Outer cover 20 may have disposed thereon one or more insert fastener components such as front and rear insert fastener components 33, 32.

Figure 3:
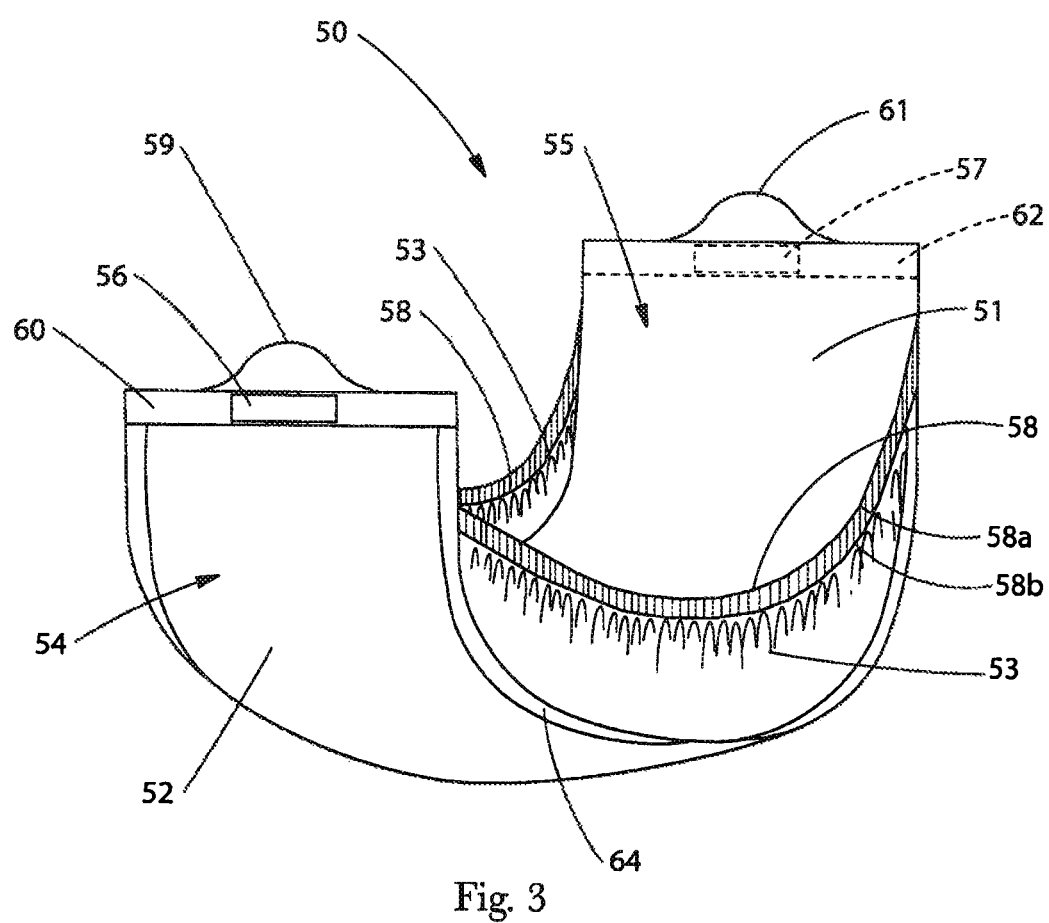
FIG. 3 is a perspective view of a disposable absorbent insert shown apart from an outer cover, as it might appear in a free-standing, relaxed state.
Figure 4:
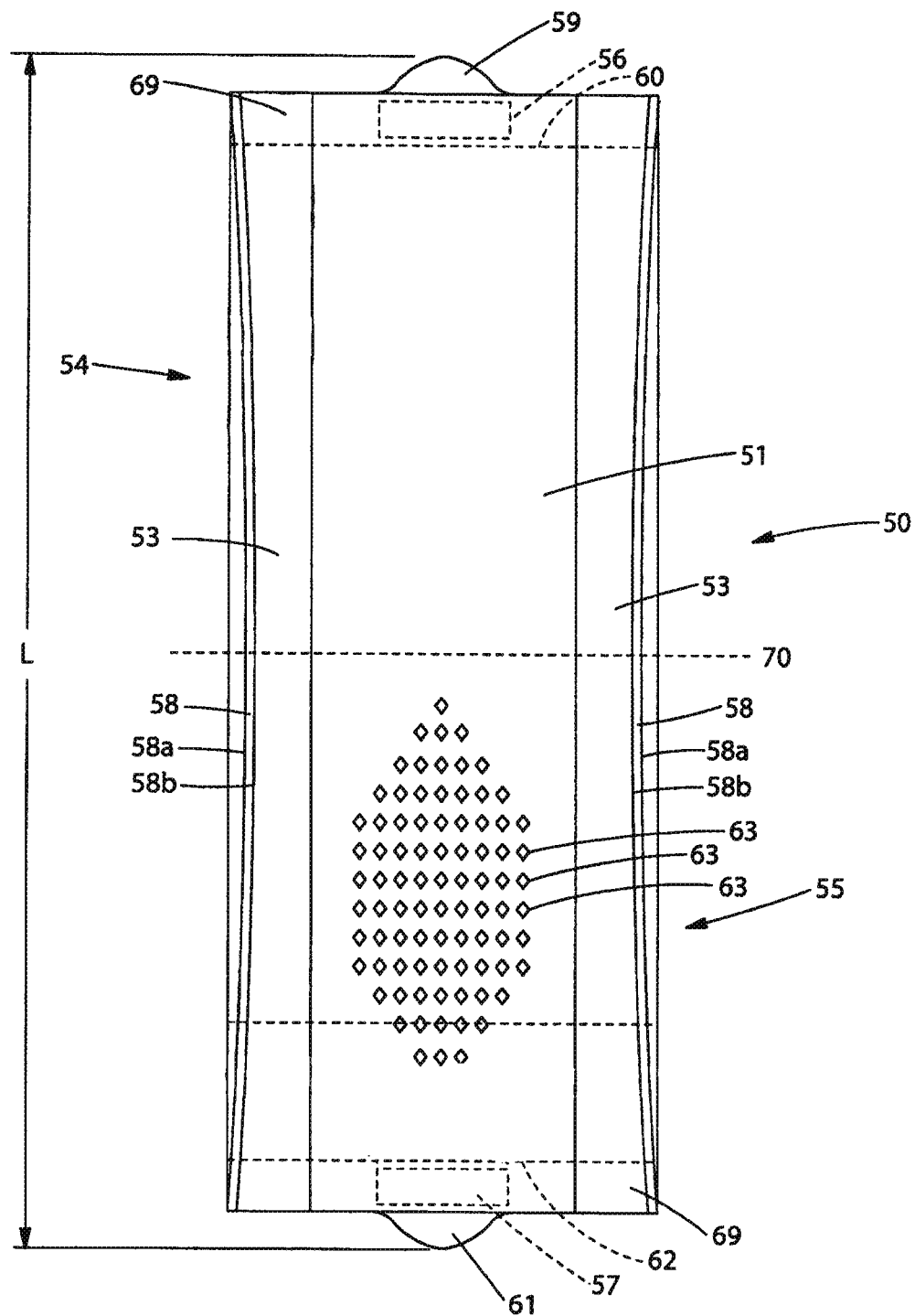
FIG. 4 is a plan view of a disposable absorbent insert shown stretched out and laid flat, body-facing surfaces facing the viewer.

FIG. 3 depicts a disposable absorbent insert 50 that may form an inner component of the wearable absorbent article 10, shown in perspective view as it might appear in a free-standing, relaxed state, apart from outer cover 20. Insert 50 may be designed to contain and/or absorb body exudates, and may be made of pliable materials as will be described further below. Insert 10 has forward region 54 and rearward region 55, and may include front fastener component 56 and rear fastener component 57. Insert 10 may include a body-facing liner or topsheet 51, outer liner or backsheet 52, and a pair of standing cuffs 53. Referring to FIG. 4, insert 50 will have a length L from the forwardmost portion of forward region 54 to the rearwardmost portion of rearward region 55, and an insert lateral axis 70 equally dividing this length. Thus, forward region 54 is forward of insert lateral axis 70, and rearward region 55 is rearward of insert lateral axis 70.

Referring to FIGS. 2B and 3, insert 50 may have rear fastener component 57 disposed thereon. Alternatively, or in addition, outer cover 20 may have rear insert fastener component 32 disposed thereon. Similarly, insert 50 may have front fastener component 56 disposed thereon. Alternatively, or in addition, outer cover 20 may have front insert fastener component 32 disposed thereon. If a two-component fastening system is used, fastener component pairs 57, 32 and 56, 33 may be cooperating components that effect fastening therebetween when these respective components are brought together. Thus, in the example depicted, in order to install absorbent insert 50 into outer cover 20, a user may lay outer cover 20 flat, inner surface 25 facing up, stretch and orient insert 50 such that rear fastener component 57 faces rear insert fastener component 32 and front fastener component 56 faces front insert fastener component 33, and bring these respective fastener component pairs 57, 32 and 56, 33 together to effect fastening therebetween.

If it is desired that outer cover 20 be reusable, for outer cover 20 to remain substantially sanitary and useful (without requiring laundering or disposal) after removal and replacement of an insert, it may be desired that all parts of outer cover 20 remain substantially unsoiled after an exudation of waste (especially fecal matter) by the wearer. Thus, it may be desired that when insert 50 is installed within an outer cover 20, there is no non-removable portion or component of outer cover 20 that lies over or covers a substantial portion of wearer-facing surfaces of insert 50 (expressed differently, no non-removable portion or component of outer cover 20 is situated between a substantial portion of insert 50 and the wearer when the wearable absorbent article is worn), at least in the areas proximate to wearer body features that discharge exudates. Thus, it may be desired that outer cover 20 include no non-removable cover sheet or the like that covers or contains substantial portions of wearer-facing surfaces of insert 50 within outer cover 20, nor any overlying structures such as pockets, straps or flaps that substantially wrap or cover the insert proximate to exudate discharge points, or lie substantially between insert 50 and the wearer's anus and/or genitals, when the wearable absorbent article is worn. If outer cover 20 lacks such overlying structures, this may increase the likelihood that the wearer's exudates will contact only insert 50, and not portions of outer cover 20.

Referring to FIGS. 1, 2A and 2B, it can be seen that wearable absorbent article 10 may be placed on a wearer by wrapping outer cover 20 between the wearer's legs and under the buttocks such that crotch region 26 is between the wearer's legs, bringing front waist edge 21 and rear waist edge 22 into the positions approximately as shown in FIG. 1, and then securing fastening ears 29 to front region 27, thereby forming a pant-like garment about the wearer as suggested in FIG. 1. When insert 50 has been installed into outer cover 20, insert 50 will then be disposed within outer cover 20, next to the wearer, with the standing cuffs 53 oriented and extending longitudinally adjacent the inner portions of leg edges 23 (i.e., longitudinally between the wearer's legs).

Examples of Possible Outer Cover Details

Fastening System

Referring to FIGS. 2A and 2B, to enable fastening of fastening ears 29 to front region 27, fastening ears 29 may have outer cover fastener components 30 disposed thereon. Alternatively, or in addition, front region 27 may have disposed thereon one or more receiving fastener components 31 disposed thereon. Fastener components 30, 31 may be selected so as to be cooperative to effect fastening of ears 29 to front region 27.

In one example, outer cover fastener components 30 may include a patch of hooks, and receiving fastener component 31 may include a patch of loops. An example of a suitable hook-and-loop fastening system is a VELCRO system (a product of Velcro Industries B.V.) A hook-and-loop fastening system provides certain advantages. Because the respective hook and loop components are supplied in sheet form, they may be cut into suitably shaped patches that can be affixed to a cloth or nonwoven substrate by various mechanisms, including adhesive bonding, mechanical bonding, ultrasonic bonding, sewing, stitching, serging, edging, and the like. If patches of hooks or loops are affixed to fastening ears 29 to form outer cover fastener components 30, as suggested by FIG. 2B, a laterally extended patch of cooperating hook or loop material can be affixed to outer cover front region 27 to form a receiving fastener component 31, as suggested by FIG. 2A. By providing for fastening of ears 29 to front region 27 at laterally varying locations thereon, this arrangement provides for easy and simple adjustability of waist opening size of the wearable absorbent article.

In another example, as noted above, the outer cover fastening system may include other types of fastener components. To provide for waist opening size adjustability, fastener components disposed on fastening ears 29 that cooperate with extended surfaces or multiple cooperating fastener components disposed on front region 27 may be used. Receiving fastener components may be multiply disposed on front region 27 in laterally arranged, varying locations, allowing for fastenability of respective ears 29 to front region 27 at laterally varying locations.

Referring to FIG. 2B, outer cover 20 also may have one or more respective fastener protectors 39 disposed thereon. This feature may prevent fastener components having features likely to randomly and unintentionally engage and catch on portions of the outer cover, or other articles, during storage, carrying, laundering and similar/related activities, from doing so, thereby avoiding potential bunching, entangling and/or damage to either outer cover 20 or other articles during such activities. For example, if fastener components 30 are patches of hooks, appropriately placed fastener protectors 39 may include patches of corresponding loops. This will enable the user to fold ears 29 over to engage them with fastener protectors 39, thereby holding them in the folded-over position such that hooks thereon will be concealed and prevented from snagging other articles when outer cover 20 is not being worn.

Outer cover 20 also includes respective front and rear visual indicia 73, 74 disposed on the front region 27 and rear region 28, respectively. Respective visual indicia disposed on insert 50 and outer cover 20 may be adapted to provide a visual cue to the user of correct/optimal orientation and placement of insert 50 within outer cover 20.

Materials

Outer cover 20 and/or layers or portions thereof may be made of any knitted, woven or nonwoven textile or textile-like material that is appropriately compatible with skin of the intended wearer(s). Outer cover 20 may be constructed of durable and/or semi-durable materials. Generally, only for purposes of reference in this description, "durable" refers to a woven or knitted textile material of any kind that may be used as a component of a washable clothing article. As used herein, "durable" includes materials which are "launderable" as defined and described in co-pending U.S. application Ser. Nos. 12/687,412, 12/687,528, and 12/687,425, entitled, respectively, "REUSABLE OUTER COVER FOR AN ABSORBENT ARTICLE," "REUSABLE OUTER COVER FOR AN ABSORBENT ARTICLE HAVING ZONES OF VARYING PROPERTIES," and "LEG AND WAISTBAND STRUCTURES FOR AN ABSORBENT ARTICLE," by Donald C. Roe, filed on the same day hereof. Generally, only for purposes of this description, "semi-durable" refers to a nonwoven material or laminate thereof that when used as an outer cover material can withstand more than one use with an insert without losing its structural integrity to an extent that renders it unserviceable. As used herein, "semi-durable" includes materials which are "laundering resistant" as defined and described in the co-pending U.S. applications identified immediately above. Thus, outer cover 20 may be constructed of materials and construction that make it reusable and/or washable.

Durable materials of which outer cover 20 may be constructed may include any natural or synthetic textile materials known in the diaper, pant, underwear, performance clothing, sport clothing, or general clothing or textile arts. Durable materials may include woven or knitted textiles made of natural fibers such as cotton, linen, wool, bamboo, hemp, silk, rayon, and the like, as well as blends of any of these fibers with any other(s), or with synthetic fibers. Examples of synthetic fibers suitable for use as components of durable materials include polyester, nylon, spandex and/or other elastomer fibers. Durable outer cover materials also may include breathable water repellent materials such as GORE-TEX (a product of W. L. Gore & Associates, Inc., Elkton, Md.), fabrics comprising microencapsulated phase-change polymer materials such as OUTLAST COMFORTEMP fabrics (products of Outlast Technologies, Boulder, Colo.—see U.S. Pat. No. 6,514,362 and U.S. Pat. No. 6,207,738, for example), COOLMAX (a product of Invista, Wichita, Kans.), and the like.

Suitable durable materials may be formed in any weave or knit fabric form, including birdseye fabric, terry, fleece, flannel, knits, stretch knits, sherpa, suedecloth, microfleece, satin, velour, Burley knits, etc. Suitable examples include POLARTECH POWER DRY, POWER STRETCH and WIND PRO (products of Polartec, LLC, Lawrence, Mass.). Knitted textiles, which may be more inherently stretchable and elastic than woven or nonwoven materials, may impart better fit, comfort and/or appearance to the outer cover. Incorporation of fibers of spandex or other elastomer also may also enhance stretchability and elasticity, and thereby impart better fit, comfort and/or appearance to the outer cover, than textiles not including such elastomeric fibers.

Specific suitable examples for durable outer cover materials include jersey knits of blends of: rayon (93%) and spandex (7%) fibers; modal (94%) and spandex (6%) fibers; cotton and spandex fibers; and bamboo and spandex fibers. Materials that have stretch capability of equal to or greater than about 2× may be desired. Suitable examples of materials may have basis weights of about 0.09-0.15 gram/in.$^2$ per layer, or other basis weights.

Durable outer cover materials may be selected to impart desired comfort, appearance and performance to outer cover 20. In some circumstances it may be desired to select durable outer cover materials which are sufficiently inexpensive to allow for disposal, if soiled extensively or damaged, with minimized issues of cost or conscience.

Semi-durable outer cover materials may include any natural or synthetic nonwoven web and/or film materials known in the diaper or pant arts. Semi-durable materials of which outer cover 20 may be constructed may include non-woven web materials of polypropylene and/or polyethylene fibers, polyester fibers, and any other synthetic fibers used to form nonwoven web materials used as components of disposable diapers, and blends thereof. Natural fibers such as cotton, linen, wool, bamboo, hemp, silk, rayon, and the like may be blended with synthetic fibers to form such a nonwoven web suitable as a component layer of outer cover 20.

Non-limiting examples of fibers, nonwovens and laminates of nonwovens and films that might be considered for use as semi-durable outer cover materials may be found in U.S. Pat. Nos. 7,223,818; 7,211,531; 7,060,149; 6,964,720; 6,905,987; 6,890,872; 6,884,494; 6,878,647; and 5,518,801; and U.S. Published Applications Nos. 2008/0319407; 2008/0045917; 2007/0293111; 2007/0287983; 2007/0287348; 2007/0249254; 2007/0203301; and 2005/0164587.

Semi-durable outer cover materials also may be selected to impart desired comfort, appearance and performance to outer cover 20. In some circumstances it also may be desired to select semi-durable outer cover materials which are sufficiently inexpensive to allow for disposal, if soiled extensively or damaged, with minimized issues of cost or conscience.

The outer cover also, or additionally, may include a laminated or substantially separate film layer, which may be elastic, to provide enhanced liquid penetration resistance and/or elastic properties. Elastic properties also can be added or enhanced via the addition of other materials to the outer cover in layer, band or strip fashion, including elastic strands, bands, scrims, and the like. A film layer may be laminated with a durable material or semi-durable material. A film layer may include an elastomer based on KRATON (a product of Kraton Polymers U.S., LLC, Houston, Tex.), or by way of further example, VISTAMAXX available from ExxonMobil Chemical Company, Houston, Tex.; FLEXAIRE, EXTRAFLEX or FABRIFLEX (products of Tredegar Film Products Corporation, Richmond, Va.), and various latex-free elastomeric sheets available from Fulflex Elastomerics Worldwide (Greenville, Tenn.).

Inclusion of an elastomeric material, either as a fibrous component of a cloth or nonwoven layer, or as a film layer, provides for improved stretchability and elasticity where it may be deemed useful to accommodate the wearer's anatomy and movements, such as over the wearer's buttocks and/or around the waist areas, and improved fit and comfort. Additionally, where a film layer may be included, it may impart additional liquid containment capability to the outer cover. A film layer may include a film that is substantially liquid impermeable, but vapor permeable, so as to provide breathability and reduce humidity within the outer cover while it is being worn, reducing chances for over-hydration of the skin where liquid containment capability is desired. A breathable film also may be provided by mechanically perforating or aperturing a film by various processes. Examples of such processes are described in co-pending U.S. application Ser. Nos. 12/366,825 and 12/534,353.

Referring to FIG. 2A, in one example outer surface 24 may be formed by a first layer of a durable or semi-durable material. The material selected may include fibers having hydrophobic properties, providing enhanced liquid containment attributes to such first layer. In another example, however, it may be desirable in some circumstances for the selected material to include hydrophilic fibers, or fibers treated to be hydrophilic, so as will cause the material to more readily absorb and/or transmit liquid therethrough. This may serve to provide supplemental absorbency within the outer cover for the event in which liquid exudates escape the insert, or to provide one way of communicating to the user that liquid exudates have escaped the insert. Additionally, in some circumstances it may be desirable that the material selected have soft tactile properties so as to have a pleasant feel that the user and/or wearer find attractive. The material also may be selected so as to have a desired appearance, including but not limited to coloration, sheen, texture, etc.

Outer cover 20 may be formed of a single layer of a durable or semi-durable material, or may have two or more layers in the front region 27 and/or rear region 28. Accordingly, referring to FIG. 2B, in another example inner surfaces 25 may be formed by a second layer of a durable or semi-durable material. The material selected may include fibers having hydrophobic properties, providing enhanced liquid containment attributes to the second layer. In another example, however, it may be desirable in some circumstances for the selected material to include hydrophilic fibers, or fibers treated to be hydrophilic. This may be desired in some circumstances to cause the material forming inner surfaces 25 to more readily absorb liquid, or transmit liquid therethrough. This may serve to provide supplemental absorbency within the outer cover for an event in which liquid exudates escape the insert, reducing the likelihood that the outer cover will leak. Alternatively, it may provide one way of communicating to the user that liquid exudates have escaped the insert, by causing wetness to be transmitted through to the outer cover outer layer such that wetness is visible on outer surfaces. Alternatively, it may serve to provide a layer that tends to draw moisture away from the skin, for a drier, more comfortable feel.

Additionally, in some circumstances it may be desirable that the material(s) selected for inner surfaces 25 have soft tactile properties so as to have a pleasant feel against the skin, particularly in areas where no portion of an insert is expected to be present between the outer cover and the wearer's skin.

In another example, the second layer of material may be formed of a textile material having enhanced elasticity, such as by inclusion of fibers of an elastomeric material (such as spandex). In another example, an intermediate film layer may be included, laminated or not laminated with another layer.

Forming the outer cover 20 of more than one layer, for example, two, or more, layers, as described above, may provide various benefits. A second layer (and any additional layers) may provide supplemental tensile strength in both the lateral and longitudinal directions across the outer cover 20. Additionally, a first layer may be selected for a first set of properties, and a second layer may be selected for a second set of properties. For example, material forming a first layer may be selected for having comparatively greater elasticity and a particular texture, color and/or other appearance-related properties, and material forming a second layer may be selected for having comparatively greater hydrophobicity, hydrophilicity and/or softness to the skin for purposes of an inner layer, the two layers in combination imparting a combination of desirable attributes to the outer cover. For example, the inner layer may be formed of material(s) and/or treated to be more hydrophilic so as to provide for absorbency and reduced chances of fluid runoff (leakage), while the outer layer may be formed of material(s) that are more hydrophobic, so as to, e.g., resist environmental soiling, or resist liquid transmission from the inner layer to the outer layer. Additionally, a plurality of layers may better serve to conceal bumps, corners, seams or other features of an insert, as compared with a single layer, for a smoother, more attractive appearance.

While the disposable insert is intended to capture and contain all wastes eliminated by the wearer in the covered region of the body, some relatively small quantities of bodily exudates, such as urine, may occasionally escape the disposable insert and contact the wearer-facing, or inner, surface of the reusable outer cover. If the inner surface of the outer cover cannot absorb the fluid, the fluid may move along the surface of the outer cover and breach the perimeter of the article, thereby leaking onto clothing or other surfaces in the environment such as bedding, carpeting, or the caregiver. While the outer cover may not be designed with an absorbent capacity as great as that of the disposable insert, the ability of the inner surface of the outer cover to quickly absorb small quantities of fluid may prevent such instances. Accordingly, the reusable outer cover may have a Centrifuge Retention Capacity of at least about 20 grams or at least about 30 or 40 grams. Since the outer cover is intended to provide the primary absorbent capacity of the article, the Centrifuge Retention Capacity of the outer cover is generally less than about 100 grams and, more typically, less than about 75 grams. Since the washing and drying of soiled outer covers requires energy, and since the number of outer covers that may fit into a typical washing machine (i.e., in one "load") is inversely related to the weight of the individual outer covers, it may be desirable to minimize the weight of the outer cover, thereby increasing the absorbent efficiency of the outer cover material. The normalized capacity of the reusable outer cover material may be at least about 1.0 g/g and may be at least about 1.5 or 2.0 g/g.

In various embodiments of the present disclosure, a reusable outer cover configured for use with a disposable absorbent insert can have an outer cover absorbent capacity, measured according to the Centrifuge Retention Capacity Test, of less than 125 grams, less than 100 grams, less than 75 grams, at least 60 grams, at least 50 grams, at least 40 grams, at least 30 grams, at least 20 grams, or any integer value for grams between any of these values, or any range formed by any of these values.

In various embodiments of the present disclosure, a reusable outer cover configured for use with a disposable absorbent insert can have an outer cover mass of less than 60 grams, less than 50 grams, less than 40 grams, less than 30 grams, less than 20 grams, or any integer value for grams between any of these values, or any range formed by any of these values.

In various embodiments of the present disclosure, a reusable outer cover configured for use with a disposable absorbent insert can have a unitized outer cover absorbent capacity, defined as the ratio of the outer cover absorbent capacity to the outer cover mass, based on any combination of outer cover absorbent capacity and outer cover mass described herein. For example, a reusable outer cover configured for use with a disposable absorbent insert, can have a unitized outer cover absorbent capacity of at least 1.0 grams per gram, at least 1.5 grams per gram, at least 2.0 grams per gram, at least 2.5 grams per gram, at least 3.0 grams per gram, or any range formed by any of these values.

Table 1, shown below, shows test data for outer cover absorbent capacity, outer cover mass, and unitized outer cover absorbent capacity from the testing of whole outer cover samples of four current market absorbent articles and from a Test Article. The four current market products were the gDiaper (size large, from gDiapers, Inc. of Portland, Oreg., United States purchased in April 210 from www.gdiapers.com), the GroBaby/Gro Via (from The Natural Baby Co. of Bozeman, Mont., United States purchased in April 2010 at www.thenaturalbabyco.com), the Bummis SuperBrite (size large, from Bummis, Inc., of Montreal, Quebec, Canada purchased in April 2010 from www.thenaturalbabyco.com), and the Diaperaps (size large, from Diaperaps: Baby's Organic Nursery, Granada Hills, Calif., United States purchased in April 2010 from www.babysorganicnursery.com).

The Test Article outer cover was configured according to embodiments of the present disclosure, with an outer cover material and inner liner material both made of 93% Modal and 7% Spandex, available as code E.n.n-14 from Koshtex, Los Angeles, Calif., United States, outer cover hooks made of 100% nylon, available as sewable hooks from Perfectek Plus, Huntington Beach, Calif., United States, outer cover landing zone, available as code 960E from Aplix, Paris, France, and insert landing zone made of 100% nylon, available as standard sew on material from Touchtape, St. Augustine, Fla., United States.

TABLE 1

| | gDiaper outer cover | GroBaby outer cover | Bummis outer cover | Diaperaps outer cover | Test Article outer cover |
|---|---|---|---|---|---|
| Whole outer cover absorbent capacity (grams) | 28.1 | 18.2 | 37.3 | 24.0 | 44.4 |

TABLE 1-continued

| | gDiaper outer cover | GroBaby outer cover | Bummis outer cover | Diaperaps outer cover | Test Article outer cover |
|---|---|---|---|---|---|
| Whole outer cover mass (grams) | 61.1 | 60.6 | 53.3 | 33.3 | 70.5 |
| Unitized whole outer cover absorbent capacity (grams/gram) | 0.46 | 0.30 | 0.70 | 0.72 | 0.63 |

For the test data in Table 1, for each type of whole outer cover, three samples were tested, and the average was reported. The outer cover mass was measured by weighing the outer cover on a scale. The outer cover absorbent capacity was measured by using the Centrifuge Retention Capacity Test, disclosed herein. The unitized outer cover absorbent capacity was calculating by dividing the outer cover absorbent capacity by the outer cover mass.

Also, for the Test Article, the unitized outer cover material absorbent capacity was measured by using the Centrifuge Retention Capacity Test and found to be 1.13 grams per gram. However, in various embodiments, it is contemplated that a reusable outer cover can be configured to have a unitized outer cover material absorbent capacity of less than 1.5, less than 1.4, less than 1.3, less than 1.2, less than 1.1, less than 1.0, less than 0.9, less than 0.8, or less than 0.7 grams per gram, or any range formed by any of these values.

In addition to forming differing layers of differing materials, it may be desirable to form a single layer of differing materials, for example, differing materials in the respective front, crotch and/or rear regions of the outer cover. Such differing materials may be joined at a seam such as inner seam 40 and/or outer seam 41. For example, the material predominately forming the inner surface of rear region 28 may be selected primarily for its elasticity features, which may better serve to provide snug fit about wearer body contours and accommodate wearer movement (i.e., about the buttocks and hips). By comparison, the material predominately forming the inner surface of front region 27 and/or crotch region 26 might be selected primarily for its hydrophobicity or hydrophilicity, which may better serve to contain liquid exudates.

Layers or other elements of the outer cover may be joined to each other via any suitable mechanism, including, for example, adhesives, mechanical bonding, ultrasonic bonding, sewing, stitching, serging, edging, and the like.

Additionally or alternatively to the constructions and materials described above, the outer cover may be constructed and may include materials and features as described in co-pending U.S. application Ser. Nos. 12/687,412, 12/687,528, and 12/687,425—entitled, respectively, "REUSABLE OUTER COVER FOR AN ABSORBENT ARTICLE," "REUSABLE OUTER COVER FOR AN ABSORBENT ARTICLE HAVING ZONES OF VARYING PROPERTIES," and "LEG AND WAISTBAND STRUCTURES FOR AN ABSORBENT ARTICLE," by Donald C. Roe, filed on the same day hereof.

Elasticized Waistbands, Leg Bands

Referring again to FIGS. 1, 2A and 2B, front waist band portion 34, rear waist band portion 35, and leg band portions 36 are depicted. One or more of these band portions 34, 35, 36 may be formed of one or more strands or strips including an elastomeric material such as spandex or a blend of spandex and other fibers, enveloped by a nonwoven or textile material, which may include the edges of the material forming the inner and/or outer layers of outer cover 20, to form and elasticize the respective band portions. The elastic material may be affixed to or within an outer cover layer in a strained condition, or at zero applied strain. Textile material(s) enveloping the elastic strand(s) or strip(s) may be sewn around elastic strand(s) or strip(s) to hold them in place within the respective band portions. If the elastic material is strained prior to, and while, being enveloped and affixed to form these band portions during the manufacturing process, upon relaxation the enveloping material and adjacent outer cover material may be caused to gather and form ruffles 37 therealong, which constitute gathered outer cover material. This can serve to promote snug fit, wearer comfort and appearance. The band portion may be disposed along the edge of the outer cover, and in some circumstances it may be desired to have the band portion situated along substantially the entire length of the leg and/or waist openings so as to form bands that substantially or completely encircle the wearer's legs and/or waist while outer cover 20 is worn. The gathered material within ruffles 37 can serve to accommodate stretching of waist band portions 34, 35 and leg band portions 36. This arrangement including elasticized leg band portions 36 as described, not only may provide for better fit about the wearer's legs, but also may enable the outer cover 20, when formed of appropriately sized and shaped material, to form a pouch-like structure 75 in the crotch region (see FIG. 1) when worn, which may serve to provide space within the outer cover to accommodate the insert 50 (FIG. 3) and help hold it in place within outer cover 20, in a substantially laterally centered position within the crotch region. This may be deemed advantageous in examples in which an insert 50 is attached within outer cover 20 by fastener components only located proximate to the respective ends of insert 50, and not at any longitudinally intermediate locations, as described further below. Alternatively, or additionally, the elastic strands or strips in waist band portions 34, 35 and leg band portions 36 may be affixed within the outer cover only at or near their respective ends, e.g., within a pouch, tube or envelope structure formed of outer cover material—referred to herein as a "drawstring elastic". This will allow the elastic material and associated outer cover material to stretch and move freely and independently of each other, which may promote fit and comfort. A snug fit about the wearer's legs provided by such elasticized leg band portions 36 may serve to enhance containment capability of the wearable absorbent article.

One or more of waist band portions 34, 35 and leg band portions 36 may be elasticized in the manner described above, or by other mechanisms. For example, elasticized band/strip material such as that used to form elastic waistbands and leg bands or other banding features of conventional cloth underwear, briefs or other articles of clothing may be separately produced, and affixed to the materials forming outer cover 20 in any suitable manner, during the manufacture thereof.

In another example, one or more of waist band portions 34, 35 and leg band portions 36 may be formed of elastic material simply affixed about the leg opening and/or waist opening edges by use of adhesive and/or compression bonding. In another example, an elastic strip material may formed by affixing a plurality of strained elastomeric strands or strips to one or more strips of unstrained nonwoven web material, or film. When the resulting elastic strip material is allowed to relax, the unstrained material forms transverse rugosities that comprise gathered unstrained material, which will accommodate stretching of the elastic strip material. By affixing the elastic strip material at one or more of waist band portions 34, 35 and/or leg band portions 36, the elastic strip material may be used to form one or more of elasticized waist band portions 34, 35 and/or leg band portions 36.

Anchoring Bands

Outer cover 20 also may include an anchoring supplement such as anchoring band 38a and 38b (collectively referred to as anchoring bands 38) disposed on or in the outer cover rear region 28 as indicated in FIGS. 2A, 2B. As suggested in FIGS. 2A and 2B, anchoring band 38 may be affixed along a layer, or disposed between layers, forming inner surfaces 25 and outer surfaces 24 of outer cover 20. Anchoring band 38 may include an elastomeric or elasticized strip or band of material, affixed to outer cover 20 at locations proximate to its rearward corners or proximate to fastening ears 29. Thus, anchoring band 38 may be partially or substantially force-decoupled from the other layer(s) of the outer cover along its lateral length from the layer(s) forming the inner and outer surfaces of outer cover 20, via attachment to the outer cover only by the ends of anchoring band 38, or only at a limited number of selected intermediate lateral locations along anchoring band 38. For example, anchoring band 38 might be attached to outer cover 20 only at the ends of anchoring band 38. In another example, anchoring band 38 might be attached to outer cover 20 only at the ends and at the lateral center of anchoring band 38. This substantially force-decoupled arrangement allows anchoring band 38 and surrounding portions of outer cover 20 to stretch and move substantially independently of one another, which may promote better fit and comfort. In another example, however, anchoring band 38 may be an elastic band, strip or strap laminated with or otherwise affixed to a layer of stretchable material forming either of or both the inner and outer surfaces of the outer cover, along substantially the entire length of anchoring band 38.

When strained laterally by application to the wearer, anchoring band 38 may serve to provide, or supplement, lateral tensile forces in the article about the wearer's waist, thereby tending to draw the waist opening snug, enhancing fit and enhancing securement of the wearable absorbent article about the wearer's waist. The elastic modulus of the anchoring band may be higher than the elastic modulus of the surrounding, adjacent, or coextensive outer cover materials.

An anchoring band, or system of one or more anchoring band members, may have any additional features described in, for example, co-pending U.S. patent application Ser. Nos. 11/810,741; 11/810,708; 12/101,476; 12/028,317; 11/810,745; 11/810,742; 11/810,734; 11/810,779; 11/810,715; 11/810,733; 11/810,736; 11/810,777; and 11/599,862; 11/810,901 and 11/599,851; 11/899,812; 12/204,844; 12/204,849; 12/204,854; 12/204,858; and 12/204,864; 11/899,810; 11/899,656; and 11/899,811; 11/899,812; 12/204,844; 12/204,849; 12/204,854; 12/204,858; and 12/204,864; and co-pending U.S. application Ser. Nos. 12/687,412, 12/687,528, and 12/687,425, entitled, respectively, "REUSABLE WEARABLE ABSORBENT ARTICLES WITH ANCHORING SYSTEMS," "REUSABLE WEARABLE ABSORBENT ARTICLES WITH ANCHORING SUBSYSTEMS," and "REUSABLE OUTER COVERS FOR WEARABLE ABSORBENT ARTICLES," by Donald C. Roe, filed on the same day hereof.

In another example, instead of, or in addition to, being oriented substantially laterally as suggested by the depicted location of anchoring band 38 in FIGS. 2A and 2B, one or more members forming anchoring bands may be oriented diagonally between the longitudinal and lateral directions. For example, as suggested in FIG. 2A, a pair of diagonal anchoring bands 38a may have respective waist ends thereof affixed at a location area proximate to corners of the outer cover and/or fastening ears 29, and respectively extend toward both the lateral and longitudinal center of outer cover 20, as suggested in FIG. 2A. The respective center ends of bands 38a may be affixed to the outer cover at locations proximate the lateral center of the outer cover as suggested in FIG. 2A, and bands 38a may be either force-decoupled or force-coupled to the outer cover along the lengths of bands 38a, as described above. In an example where an insert is connected to an anchoring band for additional longitudinal support as described further below, diagonal anchoring bands such as diagonal anchoring bands 38a may serve to provide supplementary longitudinal tension along outer cover 20, providing supplemental longitudinal support therewithin.

Examples of Possible Absorbent Insert Details

Examples of features of an absorbent insert 50 will be described with reference to FIGS. 3 and 4.

As noted above, FIG. 3 depicts a disposable absorbent insert 50 that may form an inner component of a wearable absorbent article as described herein, shown in perspective view as it might appear in a free-standing, relaxed state, apart from an outer cover. FIG. 4 depicts an example of an insert 50 shown stretched out and laid flat (against elastic-induced contraction to a position similar to that shown in FIG. 3), body-facing surfaces facing the viewer.

Insert 50 may have a topsheet 51 and backsheet 52 forming an envelope-like enclosure for absorbent core materials such as those described further below. Topsheet 51 and backsheet 52 may be affixed together along longitudinal seams, and along lateral seams 69. Insert 50 also may have longitudinal standing cuffs 53 affixed therealong.

Insert 50 also may include respective forward and rearward user grasp structures 59, 61. User grasp structures 59, 61 may be provided to enable the user to quickly and easily grasp insert 50 proximate its respective ends.

Referring to FIGS. 3 and 4, end support stiffeners 60 and 62 may be included. Such end support stiffeners may serve to aid the user in engaging the insert with the outer cover, and to help insert 50 maintain its intended shape and configuration while being worn beneath an outer cover, i.e., help maintain the intended position and gasketing function of the standing cuffs 53. End support stiffeners 60, 62 also may help control the corners of the insert regardless of the size, type or location of fastener components included on the insert. In addition to providing resistance to longitudinal pull of cuff edges 58, end support stiffeners 60, 62 may provide resistance to bending in any direction or plane.

Topsheet

Topsheet 51 may be formed of a liquid-permeable nonwoven web material. It may be desired that material forming topsheet 51 is compliant, soft-feeling, and non-irritating to the wearer's skin. It may be desired that at least a portion of topsheet 51 may be liquid pervious, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. If topsheet 51 includes fibers, the fibers may be spunbond, carded, wet-laid, meltblown, hydroentangled, or otherwise processed as is known in the art.

One suitable material comprising a nonwoven web of staple-length polypropylene fibers is manufactured by Veratec, Inc., a Division of International Paper Company, of Walpole, Mass. under the designation P-8. Additional suitable materials comprising formed films are described in U.S. Pat. Nos. 3,929,135; 4,324,246; 4,342,314; 4,463,045; and 5,006,394. Other suitable topsheets 30 may be made in accordance with U.S. Pat. Nos. 4,609,518 and 4,629,643. Suitable examples of formed and/or apertured films may include products produced by The Procter & Gamble Company of Cincinnati, Ohio as DRI-WEAVE, and by Tredegar Corporation, based in Richmond, Va., as FRESHFEEL. Suitable topsheet materials also may include laminates of films and nonwoven webs produced by Tredegar as COMFORTFEEL, COMFORTQUILT, SOFTQUILT and COMFORTAIRE.

In some circumstances it may be desired that at least a portion of topsheet 51 is made of a hydrophobic material or is treated to be hydrophobic in order to isolate the wearer's skin from liquids contained in absorbent core. If topsheet 51 is generally made of a hydrophobic material, it may be desired that at least a portion of the upper surface of topsheet 51 is treated to be hydrophilic so that liquids will transfer through the topsheet more rapidly. Topsheet 51 can be rendered hydrophilic by treating it with a surfactant or by incorporating a surfactant into the topsheet. Suitable methods for treating topsheet 51 with a surfactant include spraying the topsheet material with the surfactant and/or immersing the material into the surfactant. A more detailed discussion of such a treatment and hydrophilicity is contained in U.S. Pat. Nos. 4,988,344 and 4,988,345. A more detailed discussion of some suitable methods for incorporating a surfactant in the topsheet can be found in U.S. Statutory Invention Registration No. H1670. In another example, however, topsheet 51 may include an apertured web or film which is hydrophobic. This may be accomplished by foregoing the hydrophilizing treatment step from the production process and/or applying a hydrophobic treatment to the topsheet material, such as a polytetraflouroethylene compound like SCOTCHGUARD or a hydrophobic lotion composition, as described below. In such examples, it may be desired that the apertures be large enough to allow the penetration of aqueous fluids like urine without significant resistance otherwise attributable to hydrophobicity. It may also be desired that the apertures have sufficient effective open area and/or aperture size to allow the penetration of low-viscosity fecal material. Examples of topsheets meeting these requirements are described in U.S. Pat. Nos. 5,342,338; 6,414,215; and 6,010,491.

Any portion of topsheet 51 may be coated with a lotion or skin care composition as is known in the art. Examples of suitable lotions include those described in U.S. Pat. Nos. 5,607,760; 5,609,587; 5,635,191; 5,643,588; 5,968,025 and 6,716,441. The lotion may function alone or in combination with another agent as the hydrophobizing treatment described above.

Topsheet 51 may also include or be treated with antibacterial agents, some examples of which are disclosed in U.S. application Ser. No. 08/212,441, published as U.S. Statutory Invention Registration H1732.

Topsheet 51, backsheet 52 or any portion of the topsheet or backsheet may be embossed and/or matte finished to provide a more cloth-like appearance.

Topsheet 51 may be fully or partially elasticized or may be foreshortened so as to provide a void space between topsheet 51 and core. Exemplary structures including elasticized or foreshortened topsheets are described in more detail in U.S. Pat. Nos. 4,892,536; 4,990,147; 5,037,416; and 5,269,775.

Backsheet

Backsheet 52 is generally that outer liner portion of insert 50 forming the garment-facing surface thereof, and prevents the exudates absorbed and contained within insert 50 from wicking through and soiling the outer cover. In some circumstances it may be desired that backsheet 52 is substantially impervious to liquids.

Backsheet 52 may be formed of a film, a nonwoven, or a laminate of a film and a nonwoven. Backsheet 52 may be formed of a substantially liquid-impermeable laminate or composite of film and non-woven web. Backsheet 52 may be formed of a substantially liquid impermeable nonwoven web, or laminate of nonwoven web and substantially liquid impermeable film, so as to contain and isolate liquid exudates from the outer cover, outer clothing and/or environment of the wearer. At the same time, backsheet 52 may be vapor permeable to provide for breathability of the insert and the wearable absorbent article, reducing humidity in the areas between the insert and the wearer's body, and helping reduce the likelihood of skin irritation and/or rashes that may result from over-hydration of the skin.

The material forming backsheet 52 may include a thin plastic film such as a thermoplastic film having a thickness of about 0.012 mm (0.5 mil) to about 0.051 mm (2.0 mils). Suitable backsheet materials also may be breathable materials which permit vapors to escape while still preventing liquid from passing therethrough. Suitable examples may include those manufactured by Tredegar Corporation, based in Richmond, Va., and sold under the trade names CPC2, X15306, X10962 and X10964 film. Other examples may include microporous films such as manufactured by Mitsui Toatsu Co., of Japan under the designation ESPOIR NO and by Exxon Chemical Co., of Bay City, Tex., under the designation EXXAIRE, and monolithic films such as manufactured by Clopay Corporation, Cincinnati, Ohio under the name HYTREL blend P18-3097. Some additional examples may include breathable composite materials as described in PCT Application No. WO 95/16746; and U.S. Pat. Nos. 5,938,648; 5,865,823; and 5,571,096. In other examples, backsheet 52 may comprise elastomeric films, foams, strands, or combinations of these or other suitable materials with nonwovens or synthetic films.

In certain embodiments, the backsheet may have a water vapor transmission rate (WVTR) of greater than about 2000 $g/24\ h/m^2$, greater than about 3000 $g/24\ h/m^2$, greater than about 5000 $g/24\ h/m^2$, greater than about 6000 $g/24\ h/m^2$, greater than about 7000 $g/24\ h/m^2$, greater than about 8000 $g/24\ h/m^2$, greater than about 9000 $g/24\ h/m^2$, greater than about 10000 $g/24\ h/m^2$, greater than about 11000 $g/24\ h/m^2$, greater than about 12000 $g/24\ h/m^2$, greater than about 15000 $g/24\ h/m^2$, measured according to WSP 70.5 (08) at 37.8° C. and 60% Relative Humidity. A higher WVTR may be desired in this particular application, since the insert backsheet 52 will not form the outer surface of the wearable article, as a conventional disposable diaper backsheet would, but rather, will be covered by the one or more layers of the outer cover material(s)—which themselves may act in some circumstances to reduce WVTR of the composite structure.

Backsheet 52 may be joined to topsheet 51, absorbent core or any other element of insert 50 by any suitable attachment mechanism known in the art. For example, the attachment mechanism may include a continuous line or layer of adhesive, a patterned layer of adhesive, or an array of separate lines, spirals, or spots of adhesive. One example of an attachment mechanism comprises an open pattern network of filaments of adhesive as disclosed in U.S. Pat. No. 4,573,986. Other suitable attachment mechanisms include several lines of adhesive filaments which are swirled into a spiral pattern, as is illustrated by the apparatus and methods shown in U.S. Pat. Nos. 3,911,173; 4,785,996; and 4,842,666. Adhesives which have been found to be satisfactory are manufactured by H. B. Fuller Company of St. Paul, Minn. and marketed as HL-1620 and HL-1358-XZP. Alternatively, the attachment mechanism may comprise heat bonds, pressure bonds, ultrasonic bonds, dynamic mechanical bonds, or any other suitable attachment mechanisms or combinations of these attachment mechanisms known in the art.

It will be appreciated that the outer cover described above can be constructed of materials and construction so as to bear and sustain a majority of the structural loading generally imposed upon a disposable diaper, by stretching and accommodation of the wearer's anatomical features and body movements, and by absorption, swelling and added weight resulting from the wearer's exudations of waste. Thus, lesser requirements for structural strength of an insert might be present with use of such an outer cover, as compared with strength required of inside components of a disposable diaper. Therefore, an article such as described herein may include a disposable absorbent insert manufactured from materials that are different from those ordinarily used in the manufacture of disposable diapers, such as petroleum-derived materials, e.g., polyethylene and polypropylene. For example, a disposable absorbent insert having one or more of a topsheet, backsheet, standing cuffs and/or other components formed of products of wood, cotton, flax (linen), hemp, bamboo, or other cellulose fibers (e.g., paper), in addition to the materials identified above, is contemplated. If resistance to aqueous liquid penetration or substantial liquid impermeability is desired, e.g., for a backsheet and/or standing cuffs, a material formed of ordinarily hydrophilic fibers such as paper may be coated or impregnated with a hydrophobic material, such as a skin-compatible oil or wax, to impart the desired resistance to aqueous liquid penetration. Each of the materials forming the insert may be selected so as to be dispersible in water or an aqueous solution, flushable, biodegradable and/or compostable (preferably to an agriculturally usable humus or soil amendment).

Absorbent Core

Insert 50 may have an absorbent core within the envelope-like structure formed by topsheet 51 and backsheet 52. Absorbent core may comprise any absorbent material which is generally compressible, conformable, non-irritating to the wearer's skin, and capable of absorbing and retaining liquids such as urine and other certain body exudates. Absorbent core may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

Absorbent core may include liquid acquisition/distribution material, and storage material. Generally, acquisition/distribution material may have comparatively rapid absorption and wicking properties, but also may have limited absorption capacity. Conversely, generally, storage material may have comparatively slower absorption and wicking properties, but also may have greater absorption capacity. Thus, acquisition/distribution material may serve to rapidly absorb and distribute gushes of liquid such as urine, while storage material, having greater absorption capacity, may serve to absorb such liquid from the acquisition/distribution material and store it for the time needed until the insert may be replaced.

Absorbent wearable articles comprising at least one reusable element, such as a reusable outer cover, and one disposable element, such as a disposable absorbent insert adapted to be releasably and functionally joined to said reusable element, may be packaged together to enable a prospective user or caregiver to select an appropriate variants of each element for the intended use. For example, a package may contain one or more reusable outer covers and one or more disposable absorbent inserts adapted to be used therewith. The inserts may be specifically designed to be used with the given outer cover. For example, the outer cover may be sized for a specific range of wearers and the insert may have dimensions particularly relevant for use by a wearer of that size. Or the outer cover may have one or more fastener elements disposed on its wearer-facing surface having a type, geometry, or spacing with which one or more corresponding and complementary fastening elements on the garment-facing surface of the insert are particularly adapted to function or align. Or the absorbent capacity of the insert may be adapted to acquire and contain a large enough amount of urine from a given size wearer to enable the article to be suitable for reliable and confident overnight usage. Generally, at least about 200 grams of urine capacity, as measured by the Centrifuge Retention Capacity test disclosed herein, is required for overnight usage of disposable inserts by infant or toddler wearers. More typically, the desirable overnight capacity of a disposable insert may be at least about 225 grams, 250 grams, 300 grams, or 350 grams. In order to minimize the usage of materials, and the energy associated in their production which may contribute to global warming, it is desirable that the absorbent efficiency of the insert be as high as possible. Generally, the normalized capacity of the disposable absorbent insert is at least about 8.0 g/g, and may be at least about 10.0 g/g.

In various embodiments of the present disclosure, a disposable absorbent insert, configured for use with a reusable outer cover, can have an insert absorbent capacity, measured according to the Centrifuge Retention Capacity Test, of at least 150 grams, at least 200 grams, at least 250 grams, at least 300 grams, at least 350 grams, at least 400 grams, or any integer value for grams between any of these values, or any range formed by any of these values.

In various embodiments of the present disclosure, a disposable absorbent insert, configured for use with a reusable outer cover, can have an absorbent insert mass of less than 60 grams, less than 50 grams, less than 40 grams, less than 30 grams, less than 20 grams, or any integer value for grams between any of these values, or any range formed by any of these values.

In various embodiments of the present disclosure, a disposable absorbent insert, configured for use with a reusable outer cover, can have a unitized insert absorbent capacity, defined as the ratio of the insert absorbent capacity to the absorbent insert mass, based on any combination of insert absorbent capacity and absorbent insert mass described herein. For example, a disposable absorbent insert, configured for use with a reusable outer cover, can have a unitized insert absorbent capacity of at least 7.0 grams per gram, at least 8.0 grams per gram, at least 9.0 grams per gram, at least 10.0 grams per gram, or any range formed by any of these values.

Table 2, shown below, shows test data for insert absorbent capacity, absorbent insert mass, and unitized insert absorbent capacity from the testing of whole absorbent insert samples of two current market absorbent articles and from a Test Article. The two current market products were the gDiaper (size large, from gDiapers, Inc. of Portland, Oreg., United States purchased in April 210 from www.gdiapers.com), and the GroBaby/Gro Via (from The Natural Baby Co. of Bozeman, Mont., United States purchased in April 2010 at www.thenaturalbabyco.com).

The Test Article absorbent insert was configured according to embodiments of the present disclosure with an overall length of 400 millimeters, an overall width of 140 millimeters, 15 grams of absorbent gelling materials and about 3 grams of cellulosic fibers.

TABLE 2

| | gDiaper absorbent insert | GroBaby absorbent insert | Test Article absorbent insert |
|---|---|---|---|
| Insert absorbent capacity (grams) | 195 | 189 | 362 |
| Absorbent insert mass (grams) | 33.1 | 26.3 | 32.6 |
| Unitized insert absorbent capacity (grams/gram) | 5.90 | 7.19 | 11.09 |

For the test data in Table 2, for each type of absorbent insert, three samples were tested, and the average was reported. The absorbent insert mass was measured by weighing the absorbent insert on a scale. The insert absorbent capacity was measured by using the Centrifuge Retention Capacity Test, disclosed herein. The unitized insert absorbent capacity was calculating by dividing the insert absorbent capacity by the absorbent insert mass.

Absorbent core may be manufactured in a wide variety of sizes and shapes (e.g., rectangular, hourglass, "T"-shaped, etc.). The configuration and construction of absorbent core may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). Examples of absorbent structures for use as absorbent core may include those described in U.S. Pat. Nos. 4,610,678; 4,673,402; 4,834,735; 4,888,231; 5,137,537; 5,147,345; 5,342,338; 5,260,345; 5,387,207; and 5,625,222.

To reduce the overall size and/or thickness of the absorbent core, and thereby improve wearer comfort and reduce the volume of disposable waste created by a soiled insert, it may be desired to construct an absorbent core using the lowest volumes of core materials possible within performance constraints. Toward this end, examples of suitable materials and constructions for a suitable absorbent core are described in, but are not limited to, copending U.S. application Ser. Nos. 12/141,122; 12/141,124; 12/141,126; 12/141,128; 12/141, 130; 12/141,132; 12/141,134; 12/141,141; 12/141,143; and 12/141,146. These applications generally describe absorbent core constructions that minimize or eliminate the need for and inclusion of airfelt or other forms of cellulose fiber in combination with particles of superabsorbent polymer (hereinafter, "substantially airfelt-free cores"). Airfelt and other cellulose fiber have been used as absorbent fillers in absorbent cores of disposable diapers. Such fiber possesses absorbent properties and imparts some absorption capacity to an absorbent core, but also is included to provide a structural matrix to hold dispersed particles of superabsorbent polymer and/or absorbent gelling material. While inclusion of such particles enhances absorption capacity, keeping such particles suitably dispersed may be important to prevent the particles from "gel-blocking" in use as they swell with absorbed liquid, causing loss of absorption capacity. The inclusion of airfelt or other cellulose fiber as a matrix for superabsorbent particles can serve to reduce or prevent gel-blocking. However, it also imparts bulk to an absorbent core, even before absorption of any liquids.

An absorbent core having a portion that is substantially airfelt-free may be disposed between the topsheet 51 and the backsheet 52. The core may include a layer formed at least in part of a substrate, distributed absorbent particles of a superabsorbent polymer or absorbent gelling material, and a thermoplastic adhesive composition capturing the distributed absorbent particles and adhering to at least portions of the substrate, thereby immobilizing the absorbent particles on or proximate to, and relative to, the substrate.

Features of an outer cover 20 as described herein provide for a wearable absorbent article that has a relatively improved, garment-like (or underwear-like) fit, comfort and appearance (as an outer garment or under other clothes), as compared with many types of wholly disposable diapers currently available. If an outer cover 20 having such attributes is used with an insert 50 having an absorbent core incorporating substantial amounts of airfelt or other cellulose fiber, the improved, garment-like fit, comfort and appearance provided by the outer cover 20 may be compromised by the bulkiness of the insert. In order to better preserve some or most of the improved, garment-like fit, comfort and appearance of the outer cover 20, therefore, it may be desirable to construct absorbent core of insert 50 with features as described in one or more of patent applications cited immediately above, which provide for a relatively thin absorbent core.

In addition to providing an absorbent core having reduced bulk, the substantially airfelt-free core may generally be more flexible than an absorbent core containing substantial amounts of airfelt or other cellulose fiber. This enhanced flexibility may enable the core and the associated insert to better conform about the wearer's body when in use, providing for improved comfort and less bulky appearance of the wearable article 10.

Additionally, by reducing or eliminating airfelt or other cellulosic fiber material, the substantially airfelt-free core reduces the amount of materials consumed in manufacturing, reduces the amount of space (and in some circumstances, weight) per unit which must be packaged and shipped, conserving resources in that regard, and reduces the amount of materials and bulk which must be disposed of in connection with disposing of a used/soiled insert.

Standing Cuffs

Insert 50 also may have a pair of longitudinal standing cuffs 53 attached partially or entirely along the length thereof. Suitable longitudinal standing cuffs (in various published examples identified as "leg cuffs", "barrier cuffs" "gasketing cuffs," etc., may be formed of materials and construction such as described in, but not limited to, U.S. Pat. Nos. 6,786,895; 6,420,627; 5,911,713; 5,906,603; 5,769,838; 5,624,425; 5,021,051 and 4,597,760; and copending U.S. Published Application No. 2007/0239130 and U.S. application Ser. No. 11/195,272. As shown in FIG. 3, standing cuffs 53 may have one or more strands or strips of cuff elastics 58a, 58b disposed longitudinally therealong cuff edges 58. If such cuff elastics 58a, 58b are pre-strained prior to being affixed to the web material forming standing cuffs 53, resulting longitudinal tensile forces therealong will cause the web material forming standing cuffs 53 to gather as shown, and cause the cuffs to extend from the body of the insert (upwardly relative to FIG. 3), or causing them to "stand". This feature causes standing cuffs 53 to form a gasketing structure along the wearer's body when the article including insert 50 is worn, longitudinally on either side of the anatomical features where waste is exuded. Thus, standing cuffs 53 may serve to enhance the exudate containment capability of insert 50 and, and as a result, of the wearable absorbent article. As with backsheet 52, standing cuffs 53 may be formed of a substantially liquid impermeable web so as to contain and isolate liquid exudates from the outer cover, outer clothing and environment of the wearer. At the same time, standing cuffs 53 may be vapor permeable to provide for breathability of the insert and the wearable absorbent article, reducing humidity in the areas between the insert and the wearer's body, and helping reduce the likelihood of skin irritation and/or rashes that may result from over-hydration of the skin.

In another example, the material forming standing cuffs 53 may be integral with the material forming backsheet 52, such as described in, by way of non-limiting example, copending U.S. Published App. No. 2007/0239130. In this particular example, referring to and relative to the view in FIG. 3, a continuous piece of material may form one standing cuff 53, wrap beneath the insert to form backsheet 52, and wrap up the other side to form the other standing cuff 53. This example of a wraparound construction may provide improved liquid containment capability to insert 50, by eliminating seams along the outer liquid-containing surfaces that include standing cuffs 53 and backsheet 52. Another example of this construction is depicted and described in U.S. Pat. No. 4,808,178.

In some circumstances, however, manufacturing and/or economic constraints may discourage such construction, or else, it may be desirable for the materials forming standing cuffs 53 and backsheet 52 to have differing properties. For example, in some applications it may not be deemed necessary for standing cuffs 53 to be substantially liquid impervious, if they are otherwise formed of a nonwoven web material comprising closely situated hydrophobic fibers, which may still tend to repel and contain fluid, but may be generally more breathable than substantially liquid impervious laminates including films. In this event, improved strength and liquid containment attributes can still be imparted by having the material forming standing cuffs 53 wrap only partially beneath the lower longitudinal corners of the insert, and affixed at seams beneath the insert, rather than at its outermost lower corners as suggested by FIG. 3. One example of this construction is depicted and described in U.S. application Ser. No. 11/158,563, and in particular, FIG. 13 therein and associated descriptive text.

It is contemplated that an article of commerce including one or a plurality of outer covers and one or a plurality of inserts, as described herein, may be prepared and sold as such, as described in co-pending U.S. patent application Ser. No. 12/687,538, filed Jan. 14, 2010, and entitled, "Article of Commerce Including Two-Piece Wearable Absorbent Article," by Donald C. Roe. For example, a package containing from one to 12, or more, outer covers, together with one or a plurality of associated inserts, may be assembled and sold together as packaged. The respective outer cover(s) and inserts in a package may have matching/complementary fastening systems, orientation indicia and/or alignment indicia as described herein.

For such an article of commerce it may be desirable to determine a ratio of inserts to outer covers suitable to constitute a set of convenient numbers of outer covers and inserts, respectively. For example, it may be deemed suitable to include approximately a half day or day's supply of inserts for each outer cover included in the set. Thus, for example, the article of commerce may include inserts and outer covers in a ratio of inserts to outer covers of 1:1, 2:1, 3:1, 4:1, 5:1 or even 6:1. Accordingly, for example, a package associating a set may include one outer cover and 1, 2, 3, 4, 5 or 6 inserts; two outer covers and 2, 4, 6, 8, 10 or 12 inserts; three outer covers and 3, 6, 9, 12, 15 or 18 inserts, and so on. For a "starter" set for certain consumers such as first-time purchasers, or in other circumstances, it may be desirable for a package to contain from 2 to 14 outer covers—which may correspond roughly to from one day's to one week's supply of clean outer covers available before laundering becomes necessary.

It is also contemplated that any embodiment of absorbent inserts, as described herein, may be configured with asymmetry in any way described in co-pending U.S. patent application Ser. No. 12/687,538, filed Jan. 14, 2010, and entitled, "Article of Commerce Including Two-Piece Wearable Absorbent Article," by Donald C. Roe.

Centrifuge Retention Capacity (CRC) Test

The Centrifuge Retention Capacity (CRC) is a measure of the fluid retention capacity of a specimen submerged in 0.9% NaCl saline solution for 30 minutes and then subjected to centrifugation. The test is a based on the Worldwide Strategic Partners Standard Test Method WSP 241.2 (09), Gravimetric Determination of Fluid Retention Capacity in Saline Solution after Centrifugation.

For analysis, specimens are placed into a bag constructed from heat-sealable, water-permeable, non-apertured nonwoven. Specifications for the bag material are given in WSP 241.2 (09). Measure the length (L) and width (W) of the specimen to be tested. Cut a piece of the bag material that is 2×L+50 mm by W+25 mm. Fold the bag material in half across its width and heat-seal two of the open edges approximately 3 to 5 mm from the edges. The finished bag is L+25 mm by W+25 mm. In addition to the bags for samples, prepare three bags of the same dimensions to be used as blanks.

Outer Cover Material Sample Preparation: The outer cover article is opened and placed with the wearer-facing surface facing downward. Using scissors remove the leg elastics, such that the article can be laid flat. Identify and mark the center of a sampling region which is representative of the material making up the majority of the article, ensuring that it is free of seams, snaps, labels, etc. With a hydraulic press and cutting die (76.2 mm square±0.1 mm and 8 mm deep), cut a specimen centered on this mark through all the layers of the article, with the specimen's cut edges parallel and perpendicular to the longitudinal and lateral axis of the article. Obtain and record the dry mass of the specimen to the nearest 0.001 grams. Place all layers of the specimen into an appropriately sized bag and heat seal the remaining open edge. Prepare three replicates of each specimen for testing.

Whole Absorbent Insert Sample Preparation: Precondition samples at about 23° C.±2 C.° and about 50%±2% relative humidity for 2 hours prior to testing. The absorbent insert is unfolded and placed with the wearer-facing surface facing upward. Using scissors cut any elastic along the longitudinal edges of the article at an interval of approximately 2 cm, such that the article can be laid flat. Lay the absorbent insert on a piece of aluminum foil and cut the absorbent insert along the longitudinal and lateral axis resulting in four individual specimens. On a calibrated balance tare the weight of an appropriately sized bag. Place the specimen, and any material that fell onto the foil during cutting, into the tarred bag and heat seal the remaining open edge. Obtain and record the dry mass of the specimen to the nearest 0.001 grams. Repeat this procedure to obtain the dry mass of the three remaining specimens. Three replicate absorbent inserts are prepared for testing.

Whole Outer Cover Sample Preparation: Obtain and record the dry mass of the entire outer cover to the nearest 0.001 grams. Three replicate outer covers are prepared for testing.

Test Procedure

Obtain a pan large enough to hold several bags or specimens, and fill it with 0.9% saline solution to a level such that the bag or specimen may be completely submerged. Lay the bags or specimens to be tested onto the surface of the saline, and allow them to become wet for 1 minute before submerging. A weight placed onto the edge of the bag may be used to ensure that the sample remains submerged while allowing the solution to be freely absorbed by the specimen. After 30 minutes remove the bag or specimen from the saline solution, and immediately transfer it into the basket of a suitable centrifuge capable of subjecting the specimens to a 250 G centrifugal acceleration (such as a Clay Adams Dynac Centrifuge available from Block Scientific, Bohemia, N.Y.). Orient the specimens in the centrifuge such that the wearer-facing surface is facing outward, unless the wearer-facing surface is hydrophobic, in which case it should be oriented inward. Position the bags or specimens so that similarly weighted samples are opposite each other for proper balancing. Centrifuge the bags or specimens for 3 minutes±10 seconds at 250 G. The bags or specimens are then removed and immediately weighed. Record the wet mass of the specimen and bag, blank bag, or specimen without a bag to the nearest 0.001 grams.

Calculate the average of the three wet blank bag masses after centrifugation ($m_b$); this value is disregarded if the specimen was tested without a bag. For each specimen (i=1, 2, and 3), calculate the centrifuge retention capacity ($w_i$), expressed as a mass fraction (g/g) using the following equation:

$$w_i = ((m_{wi} - m_b) - m_{si})/m_{si}$$

Where $m_{si}$ is the mass, expressed in grams, of the dry specimen and $m_{wi}$ is the mass, expressed in grams, of the wet specimen and bag or specimen without a bag. For the absorbent inserts cut and tested as four separate specimens. Sum up the four individual masses of the dry specimens to get $m_{si}$, sum up the four individual masses of the wet specimens and bags to get $m_{wi}$, and sum up four of the average wet blank bag masses after centrifugation to get $m_b$. Use these values to calculate a total centrifuge retention capacity ($w_i$) value. Calculate and report the average centrifuge retention capacity for the three replicates to the nearest 0.001 (g/g).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross-referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended that the appended claims cover all such changes and modifications, and that nothing in the foregoing description or the figures, but rather, only the appended claims, limit the scope of the invention.

What is claimed is:

1. An absorbent article comprising:
a reusable outer cover comprising:
  a front insert fastener component: and
  a rear insert fastener component:
  wherein the reusable outer cover has:
    an outer cover absorbent capacity, measured according to the Centrifuge Retention Capacity Test;
    an outer cover mass:
    a unitized outer cover absorbent capacity, defined as the ratio of the outer cover absorbent capacity to the outer cover mass:
    wherein the unitized outer cover absorbent capacity is at least 1 gram per gram: and
a disposable absorbent insert comprising:
  a liquid impermeable backsheet;
  an insert absorbent capacity, measured according to the Centrifuge Retention Capacity Test;
  an absorbent insert mass;
  a unitized insert absorbent capacity, defined as the ratio of the insert absorbent capacity to the absorbent insert mass;
  wherein the unitized insert absorbent capacity is at least 8 grams per gram;
  a front fastener component configured to be engaged with the front insert fastener component; and
  a rear fastener component configured to be engaged with the rear insert fastener component.

2. The absorbent article of claim 1, wherein the unitized insert absorbent capacity is at least 10 grams per gram.

3. The absorbent article of claim 1, wherein the insert absorbent capacity is at least 200 grams.

4. The absorbent article of claim 1, wherein the insert absorbent capacity is at least 250 grams.

5. The absorbent article of claim 1, wherein the insert absorbent capacity is at least 300 grams.

6. The absorbent article of claim 1, wherein the insert absorbent capacity is at least 350 grams.

7. The absorbent article of claim 1, wherein the absorbent insert mass is less than 50 grams.

8. The absorbent article of claim 1, wherein the absorbent insert mass is less than 40 grams.

9. The absorbent article of claim 1, wherein the absorbent insert mass is less than 30 grams.

10. The absorbent article of claim 1, including barrier leg cuffs.

11. The absorbent article of claim 1, wherein the unitized outer cover absorbent capacity is at least 1.5 grams per gram.

12. The absorbent article of claim 1, wherein the unitized outer cover absorbent capacity is at least 2.0 grams per gram.

13. The absorbent article of claim 1, wherein the outer cover absorbent capacity is at least 40 grams.

14. The absorbent article of claim 1, wherein the outer cover absorbent capacity is at least 60 grams.

15. The absorbent article of claim 1, wherein the outer cover mass is less than 50 grams.

16. The absorbent article of claim 1, wherein the outer cover mass is less than 30 grams.

* * * * *